(12) United States Patent
Suh et al.

(10) Patent No.: US 8,563,720 B2
(45) Date of Patent: Oct. 22, 2013

(54) METHOD FOR PRODUCING IMATINIB BASE

(75) Inventors: Hearan Suh, Seoul (KR); Sang Kyu Nam, Seoul (KR); Jong Sun Lee, Yongin-si (KR); Seung Ki Kim, Suwon-si (KR)

(73) Assignee: BCWorld Pharm. Co., Ltd., Yeoju-Gun, Kyunggi-Do (KR)

(*) Notice: Subject to any disclaimer, the term of this patent is extended or adjusted under 35 U.S.C. 154(b) by 0 days.

(21) Appl. No.: 13/483,750

(22) Filed: May 30, 2012

(65) Prior Publication Data
US 2012/0330014 A1 Dec. 27, 2012

(30) Foreign Application Priority Data
May 30, 2011 (KR) .................. 10-2011-0051516

(51) Int. Cl.
*C07D 417/10* (2006.01)
(52) U.S. Cl.
USPC ............................................. 544/370
(58) Field of Classification Search
USPC ............................................. 544/370
See application file for complete search history.

(56) References Cited

FOREIGN PATENT DOCUMENTS

| KR | 10-1991-0016341 | 9/1991 |
| KR | 10-2009-0128396 A | 12/2009 |
| WO | 2008051597 A1 | 5/2008 |
| WO | 2008112722 A2 | 9/2008 |

OTHER PUBLICATIONS

Feng, 2007, Sensors and Actuators B, vol. 120, p. 665-668.*
Extended European Search Report for corresponding European Application Ser. No. 12169931.8; Sep. 12, 2012 (4 pages).

* cited by examiner

*Primary Examiner* — Yong Chu
*Assistant Examiner* — Karen Cheng
(74) *Attorney, Agent, or Firm* — Edwards Wildman Palmer LLP

(57) ABSTRACT

The present invention relates to a novel method for preparing an imatinib base, and more particularly to a method for preparing an imatinib base, which comprises reacting 4-(4-methyl-piperazinomethyl)-benzoic acid with a 2,2'-dibenzothiazolyl disulfide derivative in the presence of a phosphine derivative to prepare a novel thioester compound and preparing an imatinib base using the thioester compound as a reaction intermediate. In addition, the invention provides a novel thioester compound, which is used in the preparation of imatinib base, and a preparation method thereof. Ultimately, the invention provides a method of preparing the imatinib base in an economic manner and in high yield and purity and is expected to be used in the commercial production of large amounts of the imatinib base.

7 Claims, 4 Drawing Sheets

METHOD FOR PRODUCING IMATINIB BASE

CROSS REFERENCE TO RELATED APPLICATION

This application claims the priority to Korean Application No. 10-2011-0051516 filed on May 30, 2011, which is incorporated by reference herein.

BACKGROUND OF THE INVENTION

1. Field of the Invention

The present invention relates to a novel method for preparing an imatinib base, and more particularly to a method of preparing an imatinib base using a novel thioester compound as a reaction intermediate.

2. Description of the Prior Art

Imatinib mesylate (chemical name: 4-(4-methylpiperazin-1-ylmethyl)-N-[4-methyl-3-[(4-pyridin-3-yl)pyrimidin-2-ylamino]phenyl]benzamide mesylate) is an antitumor agent which is well known as the brand name Glivec of Novartis.

[Formula 1]

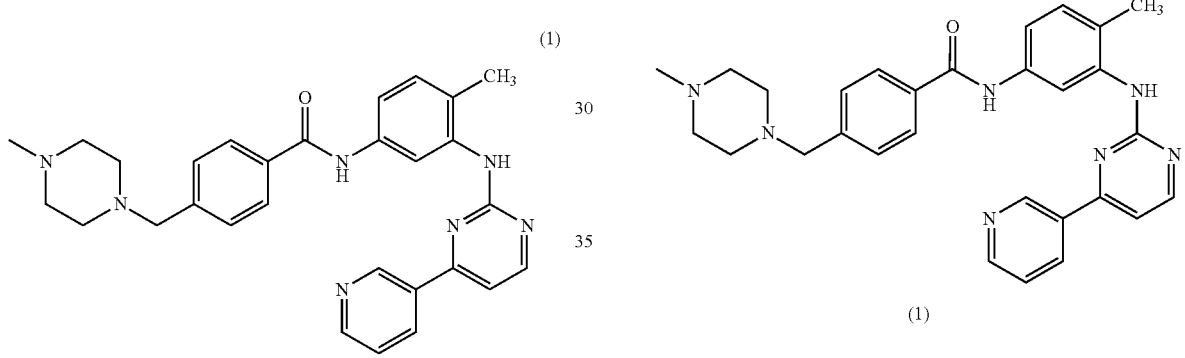

(1)

With respect to methods for preparing the compound of formula (1), which is an imatinib base, various technologies have been developed, and specific preparation methods are as follows.

Korean Patent Laid-Open Publication No. 10-1993-0005628 discloses the preparation of imatinib and the use thereof as an antitumor agent for the first time. The preparation method disclosed therein is as shown in the following reaction scheme (1).

[Reaction Scheme 1]

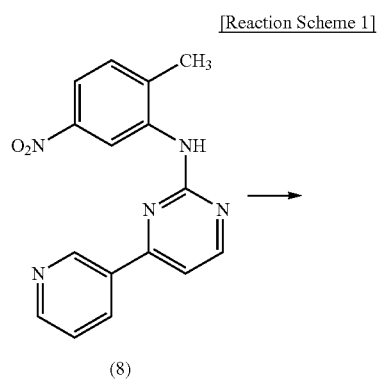

(8)

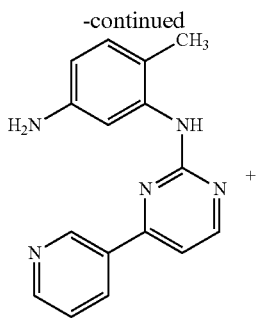

(3)

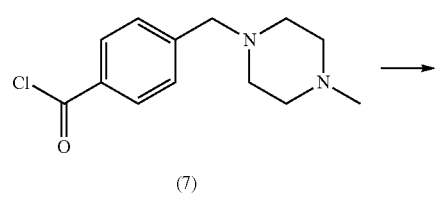

(7)

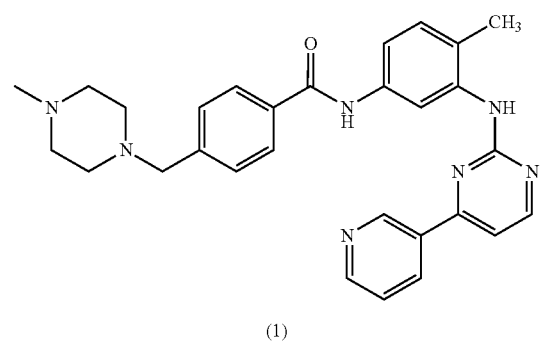

(1)

In the method shown in reaction scheme (1), a palladium catalyst is used as a reducing agent for hydrogenation in the preparation of a compound of formula (3). The process for preparing the compound of formula (3) needs to be improved, because the process yield is as low as 40-50% and the palladium catalyst is expensive.

Then, a coupling reaction between N-(5-amino-2-methylphenyl)-4-(3-pyridyl)-2-pyridinamine represented by formula (3) and 4-[(4-methyl-1-piperazinyl)methyl]benzoyl chloride represented by formula (7) is carried out to prepare a compound of formula (1).

The coupling reaction is carried out in the presence of an excess amount of pyridine, and the ratio of the pyridine to N-(5-amino-2-methylphenyl)-4-(3-pyridyl)-2-pyrimidine amine represented by formula (3) is about 138 equivalents which is equivalent to about 40 parts V/W. Then, the obtained product is purified by chromatography, but the pyridine is toxic and is not easy to remove, and the chromatography process is expensive and time-consuming, and thus is not preferred in an industrial scale process.

In a similar method, Korean Patent Laid-Open Publication No. 10-1993-0005628 discloses the use of a similar pyridine/starting amine ratio (about 140 equivalents which is equivalent to about 41 parts V/W).

In Korean Patent Laid-Open Publication No. 10-2005-018358 which discloses another similar synthetic approach, in order to prepare a compound of formula (3) from a compound of formula (8), hydrogenation with a palladium catalyst was not carried out, a chemical reduction process was carried out using stannous chloride, and the yield was also increased to 65-75%. In addition, the coupling reaction between the compound of formula (3) and the compound of formula (7) was carried out using an inactive organic solvent in place of pyridine, thus preparing the compound of formula (1). However, stannous chloride used as the reducing agent in the preparation of the compound of formula (3) is expensive. Moreover, it is described that the inactive solvent is used in place of expensive pyridine in the preparation of the compound of formula (1), but the yield and purity of the compound of formula (1) are not disclosed.

As another similar method, an improved preparation method is disclosed in Korean Patent Laid-Open Publication No. 10-2009-0061068 and is as shown in the following reaction scheme (2).

[Reaction Scheme 2]

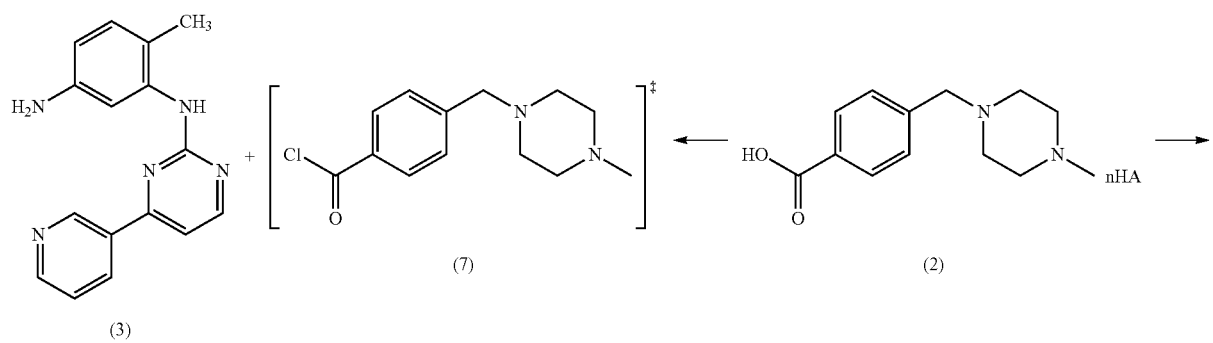

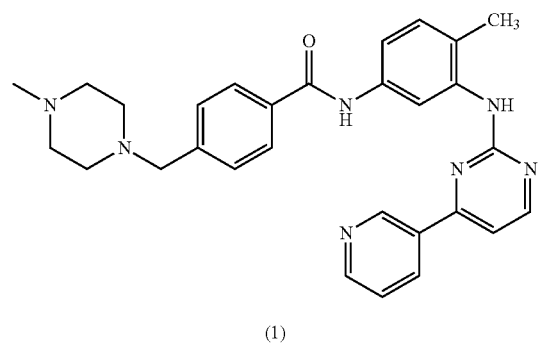

In the method shown in reaction scheme (2), a carboxylic acid of formula (2) is activated using a halogenating agent such as thionyl chloride, after which the compound of formula (7) is produced as an intermediate, and then subjected to a coupling reaction with the compound of formula (3), thus preparing the compound of formula (1). This reaction is also carried out using a pyridine solvent in an amount of about 2-10 volumes (7-35 equivalents) per gram of the compound of formula (3), and thus the resulting product contains toxic pyridine. In addition, thionyl chloride which is used as the activating agent in the preparation process generates hydrochloric acid gas and the like, which causes problem in the preparation process. Thus, this method needs to be improved.

In addition, in the above preparation process, a desmethyl impurity and the like, which are difficult to remove, are produced during the reaction. Thus, for a high-purity imatinib base, these impurities need to be removed (see Korean Patent Laid-Open Publication No. 10-2009-0061055).

Furthermore, in Korean Patent Laid-Open Publication No. 10-2009-0128396 which discloses another similar method, dicyclohexylcarbodiimide, 2-chloro-4,6-dimethoxy-1,3,5-triazine (CDMT), ethyldimethyl aminopropyl carbodiimide and 2-chloro-1,3-dimethylimidazolium chloride (DMC) were used as coupling agents with the compound of formula (2). For example, a method of preparing imatinib after producing the intermediate of formula (9) using isobutyl chloroformate is represented by the following reaction scheme (3):

of imatinib and its salts, which are used as antitumor agents for the treatment of various types of cancers, in which the method is inexpensive, consumes less time, and thus is economical, and also produces imatinib in high purity and yield.

It is an object of the present invention to provide a method for preparing a thioester compound, comprising a step of reacting a 4-[(4-methyl-1-piperazinyl)methyl]benzoic acid compound represented by the following formula (2) with a 2,2'-dibenzothiazolyl disulfide derivative represented by the

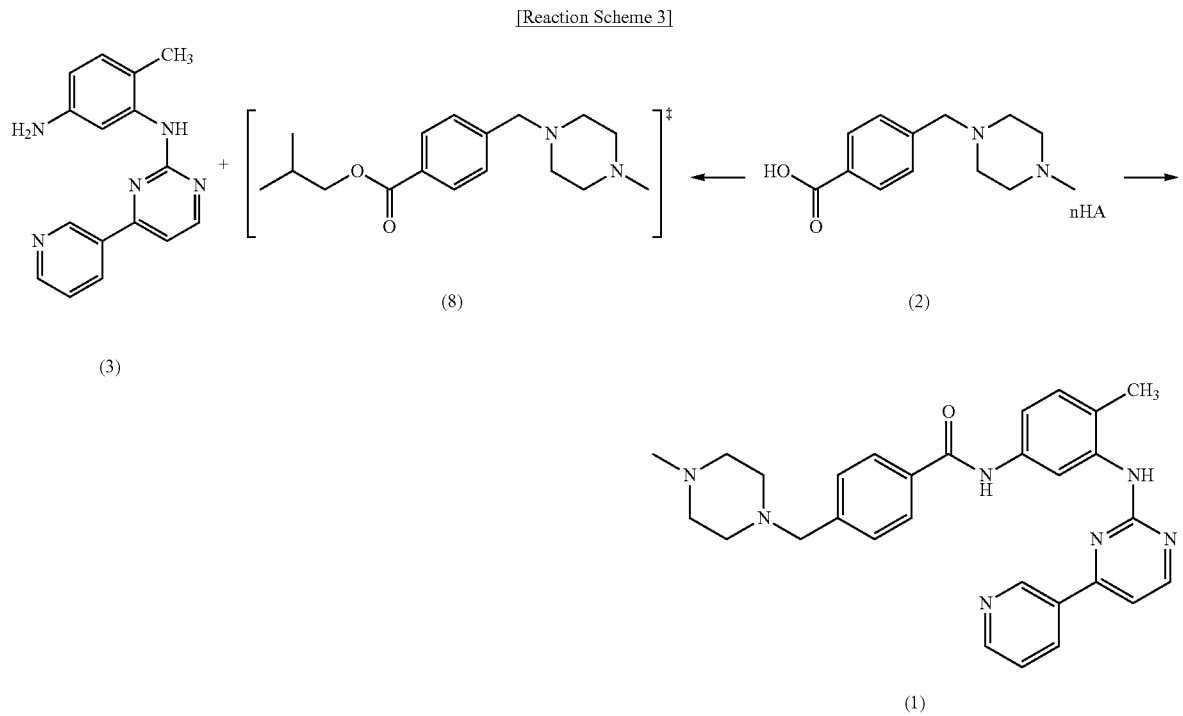

The method of reaction scheme (3) produces imatinib in a low yield of 20% or less and is disadvantageous for production of large amounts of imatinib. Thus, it needs to be improved.

Accordingly, during investigation of processes of preparing imatinib of formula (1) and pharmaceutically acceptable salts of imatinib in high purity and high efficiency, the present inventors have found that steps of activating and amidating a carboxylic acid intermediate of the following formula (4) are very important steps that determine the purity of imatinib and have examined various activating agents that selectively activate carboxylic acid from a compound of the following formula (2). As a result, the present inventors have found that the intermediate of the following formula (4) can be prepared in high purity by reacting a compound of the following formula (5) in the presence of a compound of the following formula (6), whereby a desired compound of the following formula (1) can be commercially prepared in large amounts in an economic manner and in high yield and purity, thereby completing the present invention.

SUMMARY OF THE INVENTION

The present invention is to provide a method for preparing an imatinib base, which overcomes technical problems occurring in processes of commercially producing large amounts following formula (5) in the presence of a phosphine derivative represented by the following formula (6) to prepare a novel thioester compound represented by the following formula (4), and a thioester compound prepared thereby.

Another object of the present invention is to provide a method of preparing an imatinib base represented by formula (1) in high efficiency and purity and in an economic manner by amidating a thioester compound, which is a novel intermediate represented by the following formula (4), with N-(5-amino-2-methylphenyl)-4-(3-pyridyl)-2-pyridine amine represented by formula (3).

However, objects which are to be achieved by the present invention are not limited to the above-mentioned objects, and other objects of the present invention will be clearly understood by those skilled in the art from the following description.

The present invention provides a method for preparing a thioester compound, comprising a step of reacting a 4-[(4-methyl-1-piperazinyl)methyl]benzoic acid compound represented by the following formula (2) with a 2,2'-dibenzothiazolyl disulfide derivative represented by the following formula (5) in the presence of a phosphine derivative represented by the following formula (6) to prepare a thioester compound represented by the following formula (4):

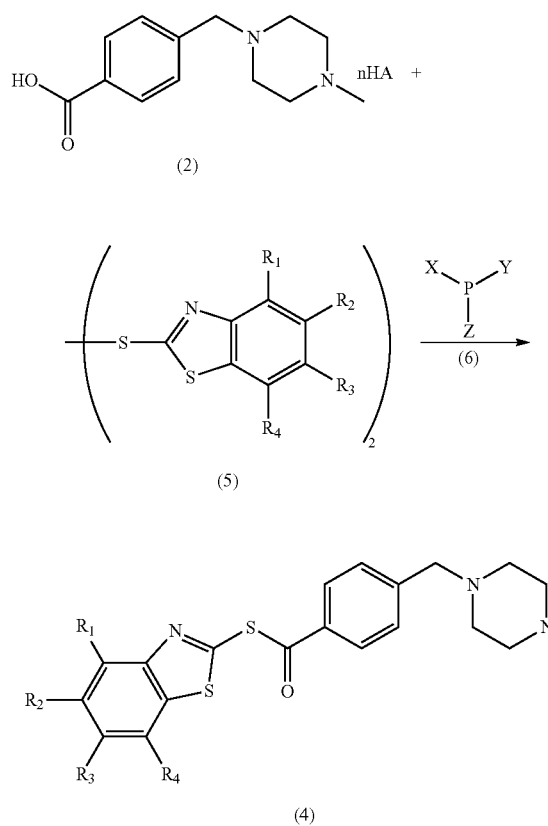

wherein HA represents an acid;
n is 0, 1 or 2;
$R_1$, $R_2$, $R_3$ and $R_4$ are each independently selected from the group consisting of hydrogen, a $C_1$-$C_6$ alkyl group, a halogen group and a nitro group; and
X, Y and Z are each independently any one of a $C_1$-$C_6$ alkyl group and a substituted or unsubstituted aryl group.

In one embodiment of the present invention, $R_1$, $R_2$, $R_3$ and $R_4$ represent hydrogen, and X, Y and Z represent a phenyl group.

In one embodiment of the present invention, the reaction in the above step may be carried out using one or more solvents selected from the group consisting of aliphatic or aromatic hydrocarbon, halogenated hydrocarbon, ether, alcohol, tetrahydrofuran, N,N-dimethylformamide, N,N-dimethylacetamide, dimethyl sulfoxide, and mixtures thereof. Preferably, the reaction solvent may be tetrahydrofuran, halogenated hydrocarbon or aromatic hydrocarbon. More preferably, it may be toluene.

In one embodiment of the present invention, the time of the reaction in said step may be 2-4 hours, and preferably 3 hours.

In one embodiment of the present invention, the 2,2'-dibenzothiazolyl disulfide derivative represented by formula (5) is used in an amount of 0.1-4.0 equivalents.

In one embodiment of the present invention, the temperature of the reaction in said step may be 0~70° C., preferably 10~60° C., and more preferably room temperature.

The present invention also provides a thioester compound prepared by said method.

The present invention also provides a method for preparing an imatinib base, comprising the steps of:

(a) reacting a 4-[(4-methyl-1-piperazinyl)methyl]benzoic acid compound represented by the following formula (2) with a 2,2'-dibenzothiazolyl disulfide derivative represented by the following formula (5) in the presence of a phosphine derivative represented by the following formula (6) to produce a thioester compound represented by the following formula (4); and (b) reacting the thioester compound represented by the following formula (4) produced in step (a) with N-(5-amino-2-methylphenyl)-4-(3-pyridyl)-2-pyridine amine represented by the following formula (3) to prepare an imatinib base represented by the following formula (1).

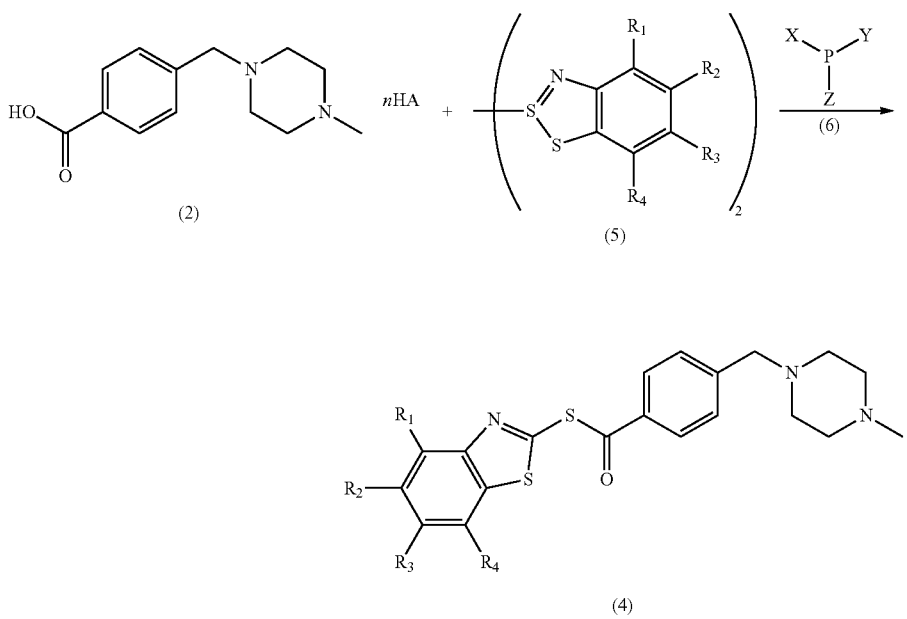

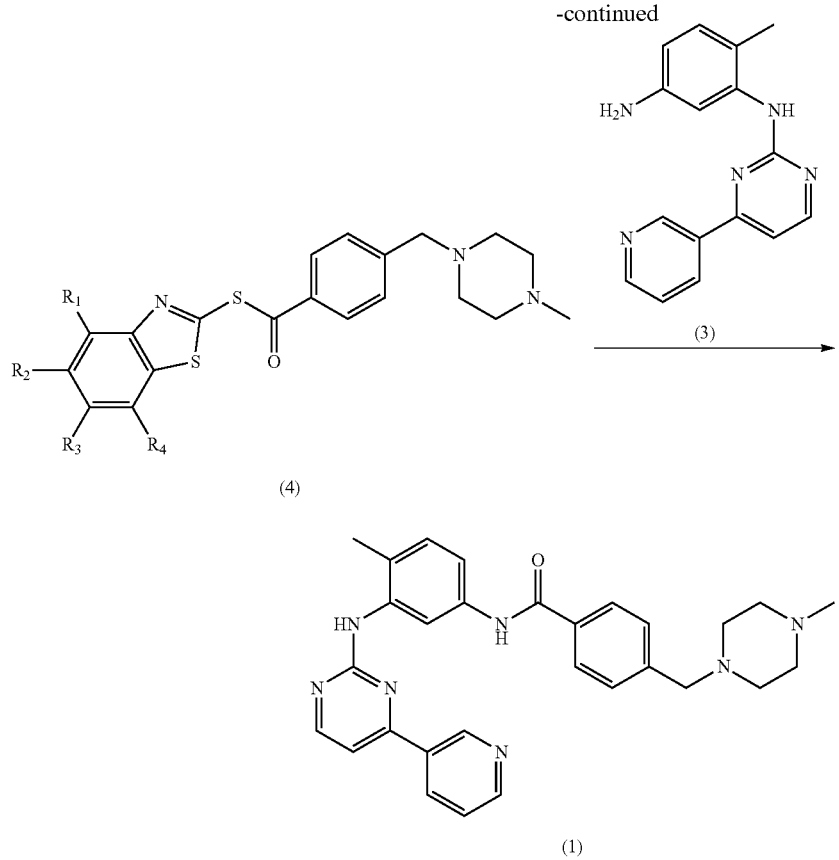

(1)

wherein HA represents an acid;

n is 0, 1 or 2;

$R_1$, $R_2$, $R_3$ and $R_4$ are each independently selected from the group consisting of hydrogen, a $C_1$-$C_6$ alkyl group, a halogen group and a nitro group; and X, Y and Z are each independently any one of a $C_1$-$C_6$ alkyl group and a substituted or unsubstituted aryl group.

In one embodiment of the present invention, $R_1$, $R_2$, $R_3$ and $R_4$ represent hydrogen, and X, Y and Z represent a phenyl group.

In one embodiment of the present invention, the reaction in step (a) or (b) may be carried out using one or more solvents selected from the group consisting of aliphatic or aromatic hydrocarbon, halogenated hydrocarbon, ether, alcohol, tetrahydrofuran, N,N-dimethylformamide, N,N-dimethylacetamide, dimethyl sulfoxide, and mixtures thereof.

In another embodiment of the present invention, the solvent may be one or more selected from the group consisting of acetone, toluene, xylene, benzene, dichloromethane, chloroform, carbon tetrachloride, methanol, ethanol, and mixtures thereof.

In one embodiment of the present invention, the time of the reaction in said step (a) may be 2-4 hours, and preferably 3 hours.

In other embodiments of the present invention, the compound of formula (5) in step (a) may be used in an amount of 0.1-4.0 equivalents, and preferably 0.9-2.0 equivalents, and the temperature of the reaction in step (a) may be 0~70° C., and preferably 10~60° C.

In another embodiment of the present invention, the compound of formula (3) in step (b) may be used in an amount of 0.1-3.0 equivalents, and preferably 0.5-2.0 equivalents, and the temperature of the reaction in step (b) may be 10~120° C., and preferably 20~60° C.

In addition, the method for preparing the imatinib base according to the present invention may further comprise the steps of (i) after completion of reaction of step (b), removing the reaction solvent to form a concentrate; (ii) dissolving the concentrate in water and adjusting a PH of the solution to 1-6; (iii) after the adjusting a pH of step (ii), removing impurities from an organic layer using an organic solvent; (iv) after the removing impurities of step (iii), adjusting a pH of the solution to 8-14; and (v) after the adjusting a PH of step (iv), producing a solid or removing a water layer using an organic solvent.

The thioester compound represented by formula (4), which is a novel intermediate that is used in the preparation of the imatinib base, may be simply prepared using compounds of the following formulas (2) and (5) as starting materials in the presence of a phosphine derivative represented by the following formula (6):

[Formula 2]

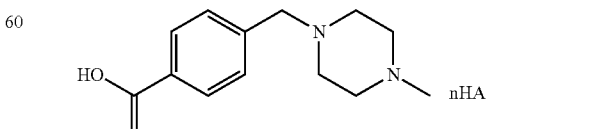

wherein HA represents an acid;

n is 0, 1 or 2;

[Formula 4]

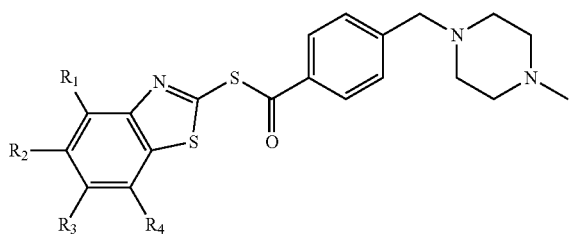

wherein $R_1$, $R_2$, $R_3$ and $R_4$ each independently represents hydrogen, a $C_1$-$C_6$ alkyl group, a halogen group and a nitro group;

[Formula 5]

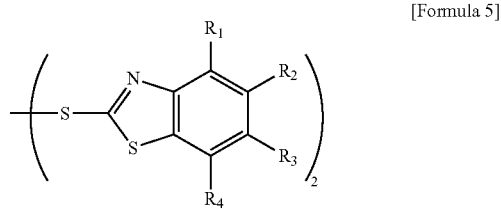

wherein $R_1$, $R_2$, $R_3$ and $R_4$ are as defined for formula (4); and

[Formula 6]

wherein X, Y and Z each independently represents a $C_1$-$C_6$ alkyl group or a substituted or unsubstituted aryl group.

DETAILED DESCRIPTION OF EXEMPLARY EMBODIMENTS

Figure 1:
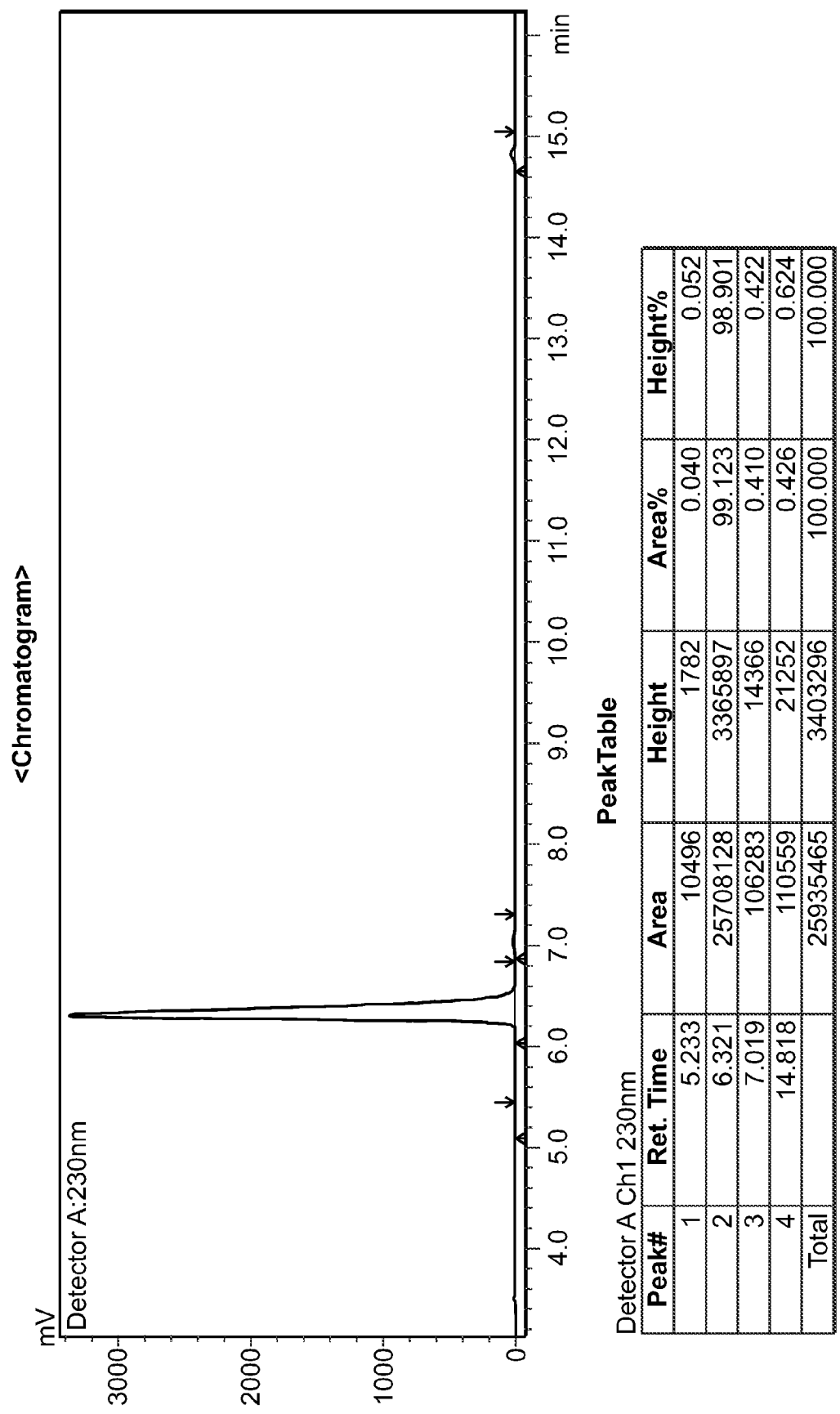
FIG. 1 shows the results of HPLC analysis of 4-[(4-methyl-1-piperazinyl)methyl]benzoic acid (formula 2) prepared in Example 1.
Figure 2:
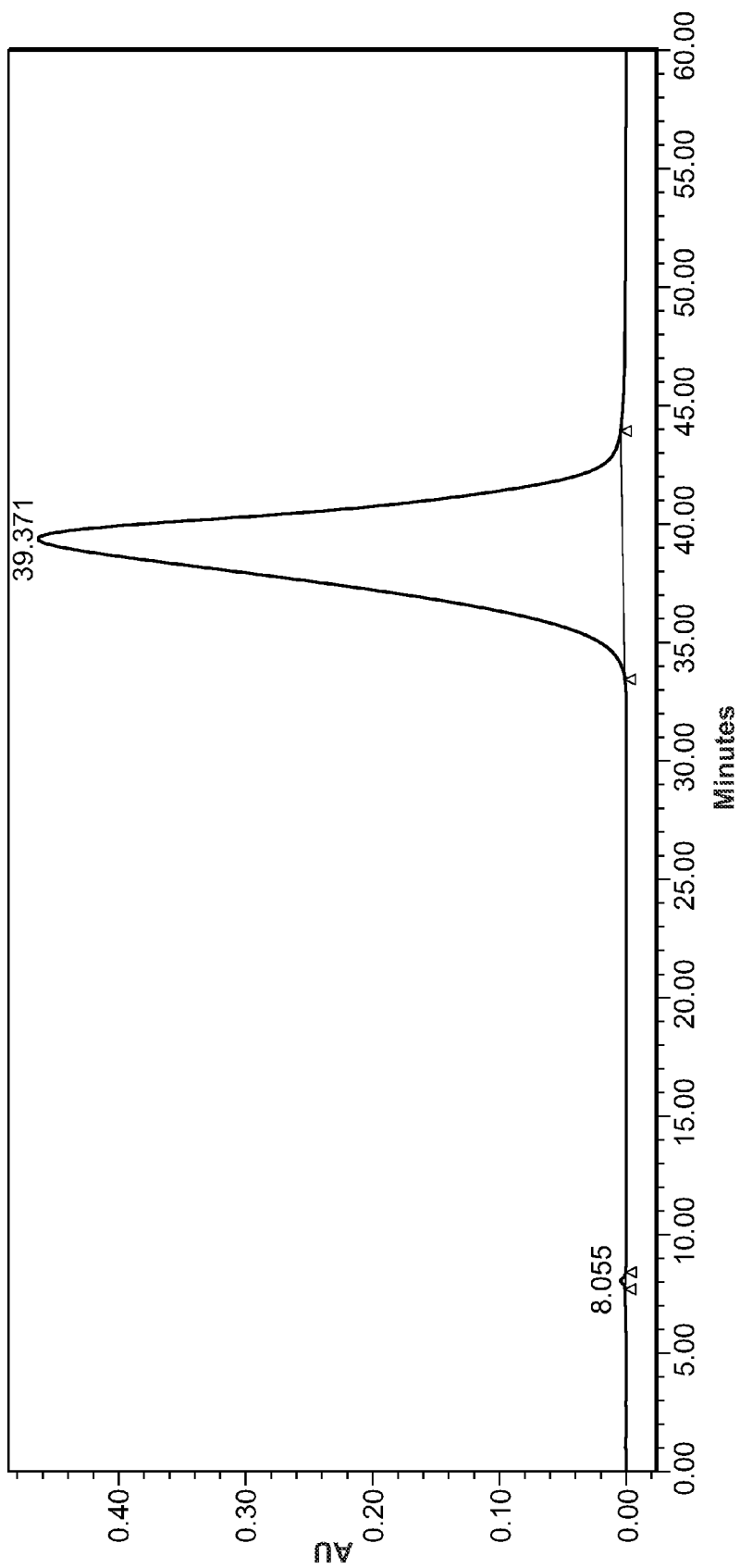
FIG. 2 shows the results of HPLC analysis of S-benzotrizol-2-yl-4-[(4-methylpiperazin-1-yl)methyl]benzoate (formula 4) prepared in Example 2.
Figure 3:
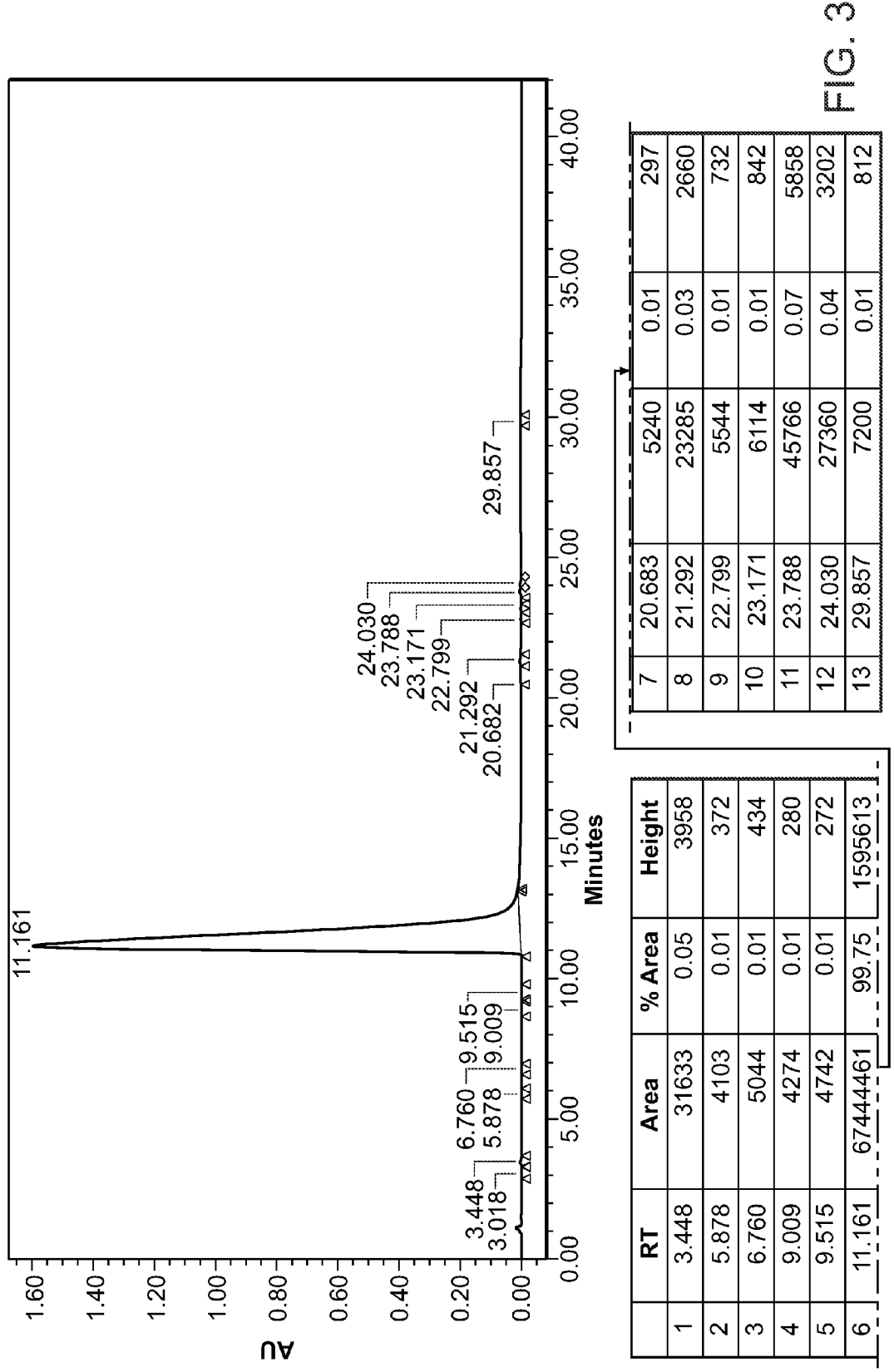
FIG. 3 shows the results of HPLC analysis of (3-{4-[4-methyl-piperazin-1-ylmethyl]benzoyl]-piperazin-1-ylmethyl}-N-[4-methyl-3-(4-pyridin-3-yl-pyrimidin-2-ylamino)-phenyl]-benzamide) (formula 1) prepared in Example 3.

Hereinafter, each step of the method for preparing the compound of formula (1) according to an embodiment of the present invention will be described in further detail.

The method for preparing the compound of formula (1) comprises the steps of:

reacting the compound of formula (2) with the compound of formula (5) in the presence of the compound of formula (6) to prepare the thioester compound of formula (4); and amidating the compound of formula (4) with the compound of formula (3) to prepare the compound of formula (1):

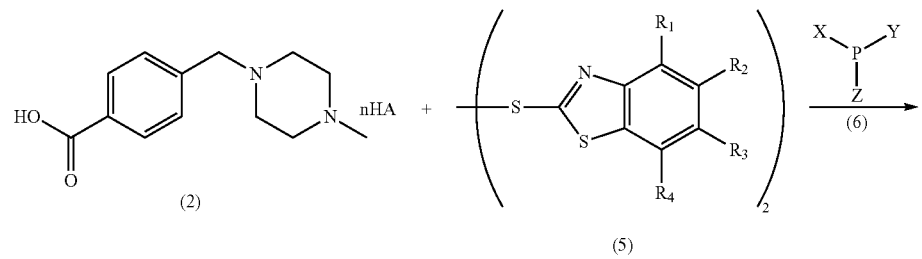

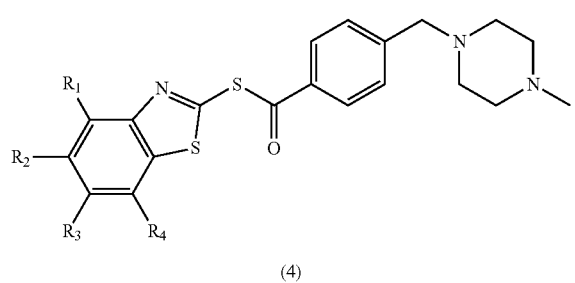

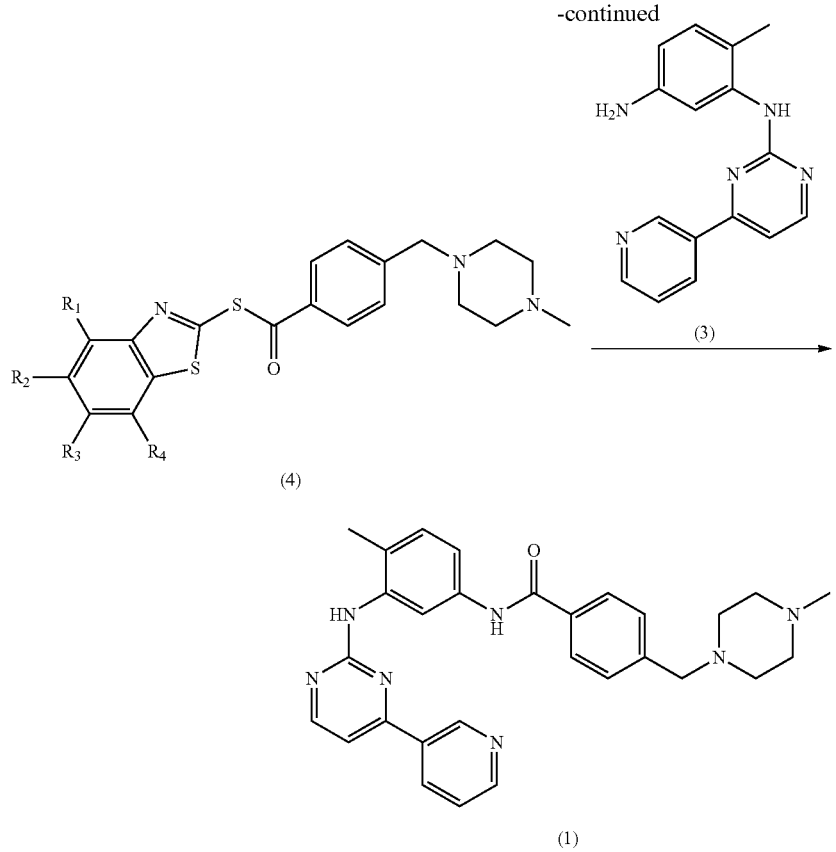

wherein HA, n, $R_1$, $R_2$, $R_3$, $R_4$, X, Y and Z are as defined above.

Step (a): Step of Preparing the Compound of Formula (4) which is Used as an Intermediate in the Preparation of the Imatinib Base A 4-[(4-methyl-1-piperazinyl)methyl]benzoic acid compound represented by the following formula (2) is reacted with a 2,2'-dibenzothiazolyl disulfide derivative represented by the following formula (5) in the presence of a phosphine derivative represented by the following formula (6) to prepare a thioester compound represented by formula (4):

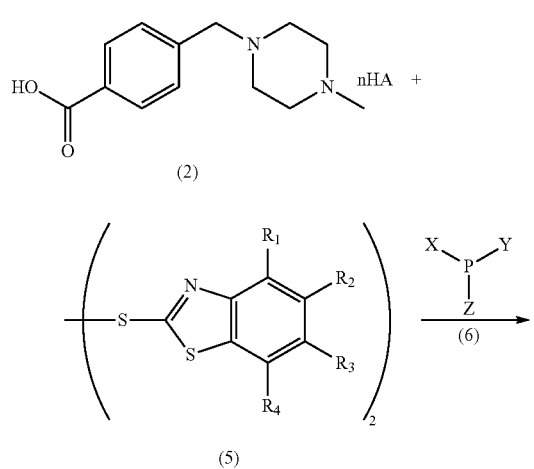

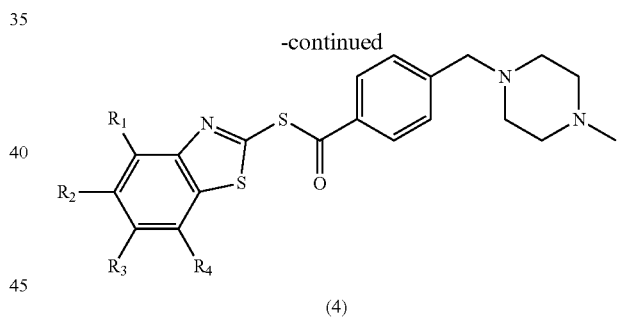

wherein HA represents an acid; n is 0, 1 or 2; $R_1$, $R_2$, $R_3$ and $R_4$ each independently represents hydrogen, a $C_1$-$C_6$ alkyl group, a halogen group and a nitro group; and X, Y and Z each independently represents a $C_1$-$C_6$ alkyl group or a substituted or unsubstituted aryl group.

In one embodiment of the present invention, $R_1$, $R_2$, $R_3$ and $R_4$ represent hydrogen, and X, Y and Z represent a phenyl group.

Examples of a solvent which is used in the above thioesterification reaction may be general aliphatic or aromatic hydrocarbon, halogenated hydrocarbon, ether, alcohol, tetrahydrofuran, N,N-dimethylformamide, N,N-dimethylacetamide, dimethylsulfoxide or the like, which may be used alone or in a mixture. Preferably, the solvent that is used in the thioesterification reaction may be one or more selected from the group consisting of acetone, toluene, xylene, benzene, dichloromethane, chloroform, carbon tetrachloride, methanol, ethanol, and mixtures thereof. More preferably, the solvent may be toluene or tetrahydrofuran.

In the above reaction, the compound of formula (5) is used in an amount of 0.1-4.0 equivalents, preferably 0.9-2.0 equivalents, and more preferably 1.0-1.2 equivalents.

In the above reaction, the compound of formula (6) may be used in an amount of 0.9-3.0 equivalents, and preferably 1.1-1.3 equivalents.

The temperature of the reaction is 0~70° C., and preferably 10~60° C.

The prepared intermediate compound represented by formula (4) may be used in the next process without further purification.

Step (B): Step of Preparing the Compound of Formula (1) by Amidation Reaction

The thioester compound of formula (4) obtained in step (a) is reacted with an N-(5-amino-2-methylphenyl)-4-(3-pyridyl)-2-pyridine amine represented by the following formula (3) to prepare an imatinib base represented by the following formula (1):

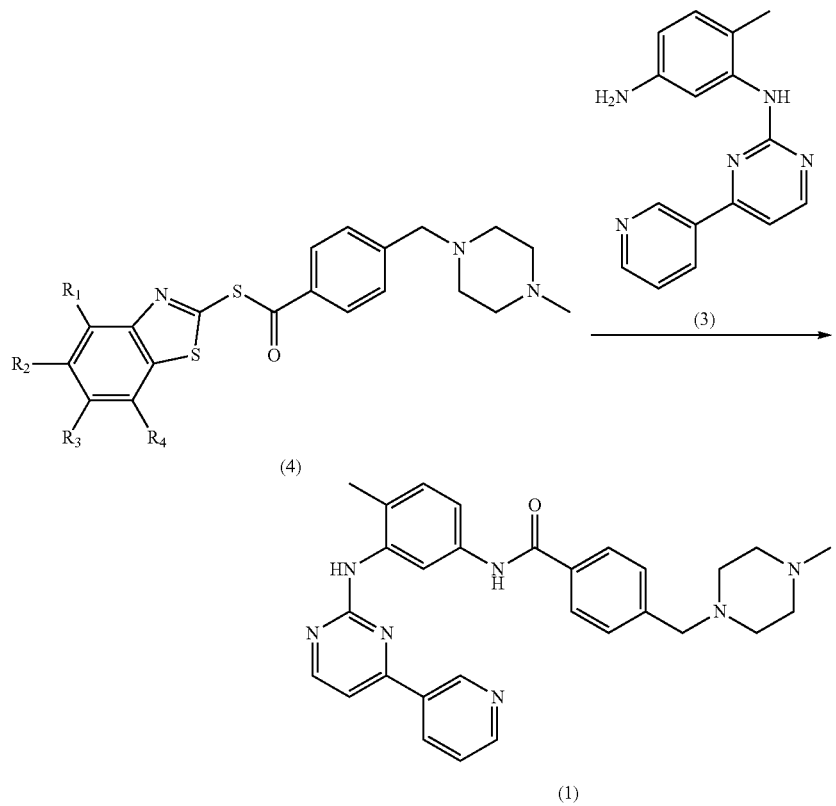

wherein $R_1$, $R_2$, $R_3$ and $R_4$ are selected from the group consisting of hydrogen, a $C_1$-$C_6$ alkyl group, a halogen group and a nitro group.

In one embodiment of the present invention, $R_1$, $R_2$, $R_3$ and $R_4$ represent hydrogen.

Example of a solvent which is used in the above amidation reaction may be general aliphatic or aromatic hydrocarbon, halogenated hydrocarbon, ether, alcohol, tetrahydrofuran, N,N-dimethylformamide, N,N-dimethylacetamide, dimethylsulfoxide and the like, which may be used alone or in a mixture. Preferably, the solvent that is used in the amidation reaction may be one or more selected from the group consisting of acetone, toluene, xylene, benzene, dichloromethane, chloroform, carbon tetrachloride, methanol, ethanol, and mixtures thereof. Most preferably, the solvent may be toluene or tetrahydrofuran.

In the amidation reaction, the compound of formula (3) is used in an amount of 0.1-3.0 equivalents, preferably 0.5-2.0 equivalents, and more preferably 0.7-1.0 equivalents, and the temperature of the reaction is 10~120° C., and more preferably 20~60° C.

Meanwhile, although the prepared compound of formula (1) may be used in the next process without purification, it may be used in the next process after purification, if necessary.

Examples of a solvent which is used in the purification process include general aliphatic or aromatic hydrocarbon, ketone, alcohol, tetrahydrofuran and the like, which may be used alone or in a mixture.

In one embodiment of the present invention, the preparation method may further comprise the steps of:

(i) after completion of reaction of step (b), removing the reaction solvent to form a concentrate;

(ii) dissolving the concentrate in water and adjusting a pH of the solution to 8-14;

(iii) after the adjusting a pH of step (ii), removing impurities from an organic layer using an organic solvent;

(iv) adding water to the organic layer and adjusting a pH of the solution to 1-6;

(v) after the adjusting a pH of step (iv), removing impurities from a water layer using an organic solvent; and (vi) adjusting a pH of the water layer to 8-14 to produce a solid and filtering the solid.

In another embodiment of the present invention, the preparation method may further comprise the steps of:

(i) after completion of reaction of step (b), removing the reaction solvent to form a concentrate;

(ii) dissolving the concentrate in water and adjusting a PH of the solution to 1-6;

(iii) after the adjusting a pH of step (ii), removing impurities from an organic layer using an organic solvent;

(iv) after the removing impurities of step (iii), adjusting a pH of the solution to 8-14; and (v) after the adjusting a PH of step (iv), producing a solid or removing a water layer using an organic solvent.

In another embodiment of the present invention, when a solid is not produced, the preparation method may comprise a step of concentrating the organic layer and producing a crystal from the concentrate using one or more solvents selected from the group consisting of water, tetrahydrofuran, alcohol, halogenated hydrocarbon, $C_1$-$C_4$-alkoxycarbonyl, $C_1$-$C_4$-alkane, $C_3$-$C_6$-cycloalkane, and mixtures thereof.

Moreover, high-purity imatinib can be obtained from the compound of formula (1) or its salt by a purification process comprising the steps of:

(i) filtering the reaction product to obtain a non-purified solid product;

(ii) dissolving the solid product with hydrochloric acid, removing impurities from the solution using an organic material, making a solid product from the impurity-removed solution using a sodium hydroxide solution, and then separating the solid product using an organic material, thereby obtaining imatinib having a purity of 99.5%;

(iii) treating the imatinib with methanesulfonic acid to obtain a imatinib salt; and (iv) neutralizing the mesylate imatinib salt and purifying the neutralized imatinib salt with hydro acid and sodium hydroxide, thereby obtaining high-purity imatinib having a purity of 99.5% or higher.

The present invention relates to a novel method for preparing an imatinib base, which can be carried out under very mild conditions in order to produce large amounts of imatinib and its various salts, particularly an imatinib mesylate salt which is used as a medical drug. In addition, the method of the present invention can be carried out in high yield by a simple purification process after each step.

In addition, in the inventive method for preparing the imatinib base, the thioester compound that is used as an intermediate is very stable, unlike an intermediate which is used in conventional preparation technology. Accordingly, the production of byproducts can be inhibited by a simple purification process, and thus high-purity imatinib having a high purity of 99.5% or more and its various salts can be obtained.

In addition, the amidating agent that is used in the present invention is commercially very stable, and the selectivity of the 4-[(4-methyl-1-piperazinyl)methyl]benzoic acid compound to carboxylic acid is very high. Thus, the amidating agent byproduct which is produced after completion of the reaction can be removed by a simple filtration process.

EXAMPLES

Hereinafter, the present invention will be described. However, the following examples and reference examples are provided for a better understanding of the present invention, and the scope of the present invention is not limited by these examples.

Reference Example 1

HPLC Analysis Conditions

Reference Example 1-1

Method for Analyzing a Compound of Formula (2) Prepared in Example 1

Process analysis for the present invention was carried out under the HPLC analysis conditions shown in Table 1 below.

TABLE 1

| | HPLC analysis conditions |
|---|---|
| Column | Sunfire C18 5 μm 250 mm × 4.6 mm Column |
| Mobile phase A | 20 mM 1-butanesulfonic acid sodium salt + 10 mM $KH_2PO_4$, pH 2.5 |
| Mobile phase B | Acetonitrile |
| Gradient | 0 min –> 5 min mobile phase B 10%, 5 min –> 20 min mobile phase B 35%, 20 min –> 25 min mobile phase B 50%, 25 min –> 40 min mobile phase B 50% |
| Flow rate | 1.0 ml/min, UV detection at 230 nm |
| Column temperature | 60° C. |

Reference Example 1-2

Method for Analyzing Compounds Other than Compound of Example 1

Process analysis for the present invention was carried out under the HPLC analysis conditions shown in Table 2 below.

TABLE 2

| | HPLC analysis conditions |
|---|---|
| Column | Symmetry C 18, 5 μm 3.9 × 150 mm |
| Mobile phase | Mobile phase A: a solution of 2.3 g of 1-octanesulfonic acid sodium salt in 700 ml of water + 300 ml of acetonitrile + 1.0 ml of phosphoric acid<br>Mobile phase B: a solution of 2.3 g of 1-octanesulfonic acid sodium salt in 100 ml of water + 900 ml of acetonitrile + 1.0 ml of 10% phosphoric acid |
| Gradient | 0 min –> 16 mobile phase A 98%, 16 –> 30 mobile phase A 50%, 30 –> 42 mobile phase A 98% |
| Flow rate | 1.0 ml/min, UV detection at 267 nm |
| Column temperature | 35° C. |

Example 1

Preparation of 4-[(4-methyl-1-piperazinyl)methyl]benzoic acid (Formula (2))

350 ml of ethanol was added to 155 g (1.547 mol) of N-methylpiperazine. At room temperature (25±3° C.), 60 g (0.351 mol) of 4-chloromethylbenzoic acid was added thereto and stirred for 6-7 hours. The reaction was analyzed by HPLC, and then the reaction solution was distilled under reduced pressure to remove ethanol, and 60 ml of 1-butanol was added thereto. The mixture was azeotropically distilled at 70±2° C. and concentrated to produce a solid. 600 ml of 2-propanol was added thereto and the mixture was stirred at room temperature (25±3° C.) for 30 minutes, stirred under reflux for 15 minutes, and then stirred at room temperature (25±3° C.) for 12 hours with slow cooling. The produced precipitate was cooled to 19±3° C., stirred for 1 hour and then filtered. The filtrate was washed with 50 ml of cooled 2-propanol and dried in an oven at 60° C., thereby obtaining a white compound of formula (2) (60 g, yield: 72%, purity: 95% or higher).

HPLC purity: 99.123% (desmethyl impurity: 0.042%, starting material 0.42%).

Thin layer chromatography: Methanol-Dichloromethane (7:5), Rf: 0.2.

Example 2

Preparation of S-benzotrizol-2-yl-4-[(4-methylpiperazin-1-yl)methyl]benzoate (Formula (4))

In a 100-ml round bottom flask, triphenylphosphine (2.39 g, 9.113 mmol) was dissolved in toluene (32 ml). At room temperature (25±3° C.), 2,2'-dibenzothiazolyl disulfide (2.92 g, 8.792 mmol) was added thereto and stirred at room temperature (25±3° C.) for 20 minutes. To the reaction solution, 4-[(4-methyl-1-piperazinyl)methyl]benzoic acid (2.0 g, 8.536 mmol) was added slowly (generation of heat of about 3° C.). Then, the reaction solution was stirred at room temperature (25±3° C.) for 3 hours and analyzed by HPLC. After completion of the reaction, the reaction temperature was cooled to 0° C., and the produced precipitate was filtered and then washed with 2 ml of cooled toluene, thereby obtaining 2.66 g of a white crystal compound of formula (6) (2.66 g, yield: 85%).

HPLC purity: 99.93%

Thin layer chromatography: Methanol-Dichloromethane (7:5), Rf: 0.3.

Example 3

Preparation of (3-{4-[4-methyl-piperazin-1-ylmethyl]benzoyl]-piperazin-1-ylmethyl}-N-[4-methyl-3-(4-pyridin-3-yl-pyrimidin-2-ylamino)-phenyl]-benzamide) (Formula (1))

The compound of formula 4 obtained in Example 2 was dissolved in 30 ml of toluene to form a slurry, and at room temperature (25±3° C.), N-(5-amino-2-methylphenyl)-4-(3-pyridyl)-2-pyridine amine (1.79 g, 6.487 mmol) was added dropwise thereto. The mixture was stirred at 50±5° C. for 3-4 hours. The reaction was analyzed by HPLC, and then the reaction solution was cooled to 10~15° C. and stirred for 30 minutes. The produced solid was filtered and washed twice with 3 ml of cooled toluene. 28 ml of water was added to the filtered solid, and about 9 ml of 3N-Hydrochloric acid solution was slowly added dropwise thereto with stirring at 25° C. to adjust the solid solution to a pH of 3-4. Then, the solid solution was washed three times with 36 ml of chloroform. The water layer was adjusted to a pH of 9-12 with about 24 ml of 1N-Sodium hydroxide aqueous solution and separated into layers by addition of 36 ml of chloroform. The organic layer was dried over Sodium sulfate, filtered and concentrated under reduced pressure. The concentrate was dissolved in 10 ml of ethyl acetate, stirred at room temperature for 15 minutes, and filtered. The obtained solid was dried at 60° C., thereby obtaining 2.89 g of imatinib (2.89 g, yield: 80.15%, purity: 99.56%).

HPLC purity: 99.75%.

Thin layer chromatography:Methanol-Dichloromethane (1:9). Rf: 0.2.

Example 4

Preparation of (3-{4-[4-methyl-piperazin-1-ylmethyl]benzoyl]-piperazin-1-ylmethyl}-N-[4-methyl-3-(4-pyridin-3-yl-pyrimidin-2-ylamino)-phenyl]-benzamide) (Formula (1))

In a 100-ml round bottom flask, triphenylphosphine (4.98 g) of formula (6) was dissolved in toluene (74.0 ml). At room temperature (25±5° C.), 2,2"-dibenzothiazolyl disulfide (6.08 g) of formula (5) was added thereto and stirred for 20 minutes. To the reaction solution, 4-[4-methyl-1-piperazinyl)methyl]benzoic acid (4.16 g) of formula (2) was added slowly. At the same temperature, the mixture was stirred for 2-3 hours. After completion of the reaction, a compound (3.74 g) of formula (3) was added slowly to the reaction solution, and the mixture was then heated to 50±5° C., stirred at that temperature for 3-5 hours, and then stirred until cooled to 25° C. Then, the stirred solution was cooled to 12.5±2.5° C., and the produced solid was filtered and washed with toluene (7.2 g), thereby obtaining a light yellow solid.

To the filtered solid, a mixed solvent of water (83.2 g)/Dichloromethane (110.3 g) was added to form a slurry. The slurry was adjusted to a pH of 3.5 using 3N-Hydrochloric acid, stirred for 10 minutes and then allowed to stand. The separated organic layer was removed, and an insoluble material of the intermediate layer was filtered through paper together with the water layer. The water layer was washed with 2-Butanol (67.1 g). The water layer was prepared, Dichloromethane (110.3 g) was added thereto, and the mixture was adjusted to a pH of 12 with 1N-NaOH solution. Then, the solution was separated into layers, and the organic layer was dried with $Na_2SO_4$ (4.16 g). The residue was filtered and concentrated, thereby obtaining a light yellow solid.

The obtained solid was added to acetone (65.7 g) and refluxed for 30 minutes. The refluxed material was cooled at 25±5° C., filtered, washed with acetone (6.57 g) and dried with hot air at 40° C. for 3 hours, thereby obtaining a light yellow solid.

The obtained solid was dissolved in a mixed solvent of Dichloromethane (27.6 g)/Methanol (32.9 g) and then filtered to remove impurities. The filtrate was concentrated and re-concentrated with acetone (6.57 g). The concentrate was refluxed in acetone (65.7 g) for 2 hours. The refluxed material was cooled to 25±5° C., filtered with acetone (6.57 g) and dried with hot air at 40° C. for 12 hours, thereby obtaining an imatinib base (4.01 g, 62.5% yield, HPLC purity: 99.91%) as a light yellow solid.

Thin layer chromatography: Methanol-Dichloromethane (1:9). Rf: 0.2.

Figure 4:
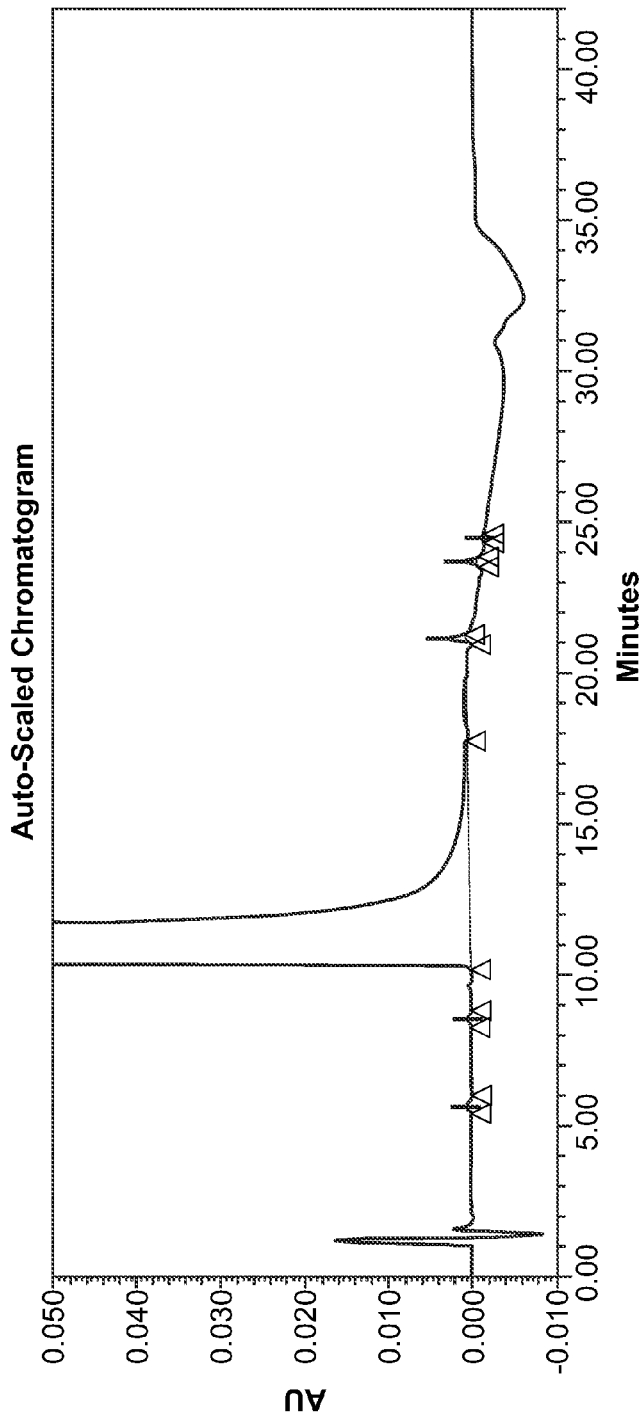
FIG. 4 shows the results of HPLC analysis of (3-{4-[4-methyl-piperazin-1-ylmethyl]benzoyl]-piperazin-1-ylmethyl}-N-[4-methyl-3-(4-pyridin-3-yl-pyrimidin-2-ylamino)-phenyl]-benzamide) (formula 1) prepared in Example 4.

As can be seen in FIG. 4, the compound of formula (1) had a high HPLC purity of 99.91% (see FIG. 4).

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive.

What is claimed is:

1. A method for preparing a thioester compound, comprising a step of reacting a 4-[(4-methyl-1-piperazinyl)methyl]benzoic acid compound represented by the following formula (2) with a 2,2'-dibenzothiazolyl disulfide derivative represented by the following formula (5) in a reaction solvent selected from the group consisting of tetrahydrofuran, halogenated hydrocarbon, aromatic hydrocarbon, and mixtures thereof, in the presence of a phosphine derivative represented by the following formula (6), thereby preparing a thioester compound represented by the following formula (4):

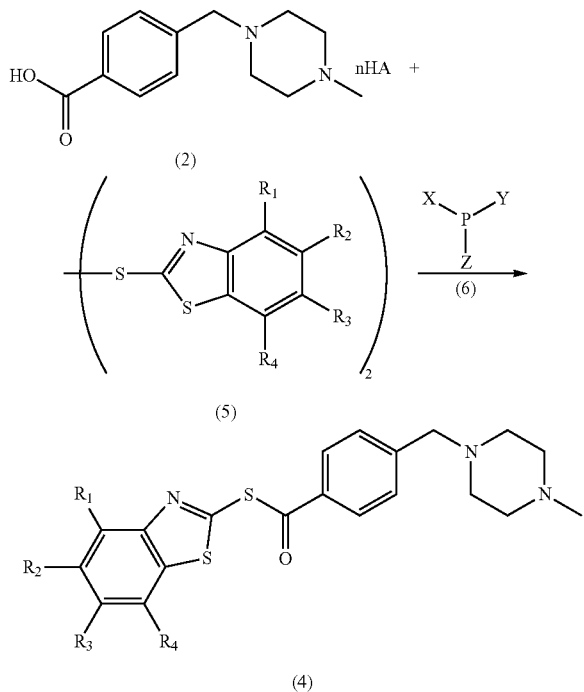

wherein HA represents an acid;
n is 0, 1 or 2;
$R_1$, $R_2$, $R_3$ and $R_4$ represent hydrogen; and
X, Y and Z represent a phenyl group.

2. The method of claim 1, wherein the reaction solvent is selected from the group consisting of toluene, xylene, benzene, dichloromethane, chloroform, carbon tetrachloride, and mixtures thereof.

3. The method of claim 1, wherein the reaction in the step is carried out for 2-4 hours.

4. The method of claim 3, wherein the reaction in the step is carried out for 3 hours.

5. The method of claim 1, wherein the 2,2'-dibenzothiazolyl disulfide derivative represented by formula (5) is used in an amount of 0.1-4.0 equivalents.

6. The method of claim 1, wherein the reaction in the step is carried out at a temperature between 10° C. and 60° C.

7. A thioester compound represented by the following formula (4) prepared by the method according to claim 1:

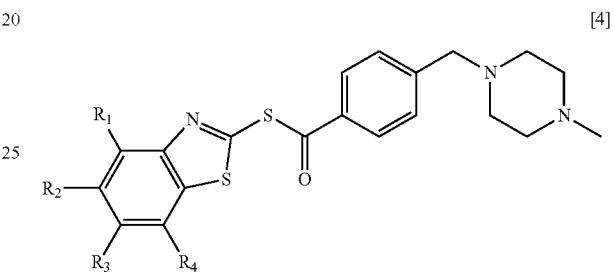

wherein $R_1$, $R_2$, $R_3$ and $R_4$ represent hydrogen.

* * * * *